United States Patent [19]

Inoue et al.

[11] Patent Number: 4,504,679

[45] Date of Patent: Mar. 12, 1985

[54] PROCESS FOR SYNTHESIZING UREA

[75] Inventors: Shigeru Inoue, Kamakura; Hiroshi Ono, Fujisawa; Akito Fukui, Inba; Hidetsugu Fujii, Mobara; Haruyuki Morikawa, Funabashi; Suguru Watanabe, Chiba, all of Japan

[73] Assignee: Toyo Engineering Corporation, Tokyo, Japan

[21] Appl. No.: 430,557

[22] Filed: Sep. 30, 1982

[30] Foreign Application Priority Data

Oct. 16, 1981 [JP] Japan .................................. 56-164150

[51] Int. Cl.$^3$ ............................................. C07C 126/02
[52] U.S. Cl. ........................................ 564/67; 564/70; 564/71; 564/72
[58] Field of Search .............................. 564/67, 71, 72

[56] References Cited

U.S. PATENT DOCUMENTS

| | | | |
|---|---|---|---|
| 3,944,605 | 3/1976 | Inoue et al. | 564/71 |
| 3,952,055 | 4/1976 | Mavrovic | 564/67 |
| 4,053,507 | 10/1977 | Inoue et al. | 564/71 |
| 4,081,469 | 3/1978 | Ono et al. | 564/71 |
| 4,088,684 | 5/1978 | Mavrovic | 564/71 |
| 4,110,374 | 8/1978 | Inoue | 564/71 |
| 4,296,252 | 11/1981 | Mavrovic | 564/71 X |
| 4,334,096 | 6/1982 | Konoki et al. | 564/72 |
| 4,354,040 | 10/1982 | Inoue et al. | 564/72 X |

Primary Examiner—Robert V. Hines
Attorney, Agent, or Firm—Flynn, Thiel, Boutell & Tanis

[57] ABSTRACT

Disclosed herein is a process of synthesizing urea including reacting ammonia and carbon dioxide at a urea synthesis pressure and temperature in a urea synthesis zone, separating excess ammonia and unreacted ammonium carbamate from the thus-obtained urea synthesis melt as a gaseous mixture containing ammonia and carbon dioxide, recirculating the gaseous mixture to the urea synthesis zone, and, on the other hand, obtaining urea from an aqueous urea solution which has been obtained by separating the excess ammonia and unreacted ammonium carbamate. The above process features ingeniously combined conditions of various process steps. It produces urea using less high-pressure steam and recovers less low-pressure steam. A stripping operation making use of carbon dioxide can be effectively incorporated in the above process. The above process permits to cut the construction cost of a urea synthesis plant.

5 Claims, 2 Drawing Figures

PROCESS FOR SYNTHESIZING UREA

BACKGROUND OF THE INVENTION (a) Field of the Invention

This invention relates to an improved process for synthesizing urea, and more specifically to a process for synthesizing urea which process features improved thermal economy.

(b) Description of the Prior Art

With the skyrocketing energy prices in recent years, thorough recovery of thermal energy has also been attempted in the production of urea so as to reutilize the thus-recovered thermal energy in the urea synthesis system and, when there is any surplus thermal energy left, to reclaim it as low-pressure steam. Steam consumption in each production process of urea is expressed in terms of a difference between the thus-reclaimed low-pressure steam and high-pressure steam which has been required for the separation of unreacted substances in the system. As the above difference becomes smaller, the production process of urea is considered to have been improved further.

The so-called stripping process is known as one of processes of the above-described type. In this particular process, unreacted ammonium carbamate and excess ammonia (hereinafter called generically "unreacted substances") in a urea synthesis melt are stripped by carbon dioxide or ammonia supplied as a raw material under the same pressure as the urea synthesis pressure while heating same with high-pressure steam of 20 kg/cm²G or higher, thereby to decompose and separate the unreacted substances. A resulting gaseous mixture consisting of the thus-separated ammonia and carbon dioxide as well as carbon dioxide or ammonia which has been employed as a stripping gas for the decomposition and separation of the unreacted substances is condensed at substantially the same pressure and the resulting heat is recovered as low-pressure steam at 2–5 kg/cm²G. The thus-produced steam is so much that a surplus of steam is still left even after it has been used in every steps of the urea synthesis system which steps are capable of utilizing such steam, for example, in the concentration step. On the other hand, a urea synthesis effluent which has been obtained by decomposing and separating unreacted substances with carbon dioxide is subjected to a low-pressure decomposition operation of 1–5 kg/cm²G so as to decompose and remove substantially all the remaining unreacted substances. Furthermore, a urea synthesis effluent which has been obtained by decomposing and removing unreacted substances with ammonia still contains lots of ammonia therein. It is thus subjected to a medium-pressure decomposition operation of 10–25 kg/cm²G, followed by subjecting the resulting stream to a low pressure decomposition operation of 1–5 kg/cm²G. High to low pressure steam is used as a heat source for such medium-pressure and low-pressure decomposition operations. As a general rule, lots of low-pressure steam are recovered in the above-described stripping process but a large amount of high-pressure steam is on the other hand consumed in the stripping process, because, although the stripping operation in a stripping process becomes easier to practice as its pressure decreases, a urea synthesis melt obtained by conducting the synthesis of urea under low urea synthesis pressures has a poor urea synthesis yield and contains lots of unreacted substances and more high-pressure steam is required for the decomposition and separation of such unreacted substances.

In order to avoid such a difficulty as described above, it becomes necessary to conduct the synthesis of urea using ammonia in a still higher excess proportion and raising the urea synthesis pressure and temperature further. However, use of a higher urea synthesis pressure creates another difficulty, because the stripping operation has to be carried out at a higher pressure. Of course, it is possible to conduct the stripping operation at higher temperatures so as to facilitate the stripping operation. However, high-temperature stripping results in a drawback that more of the resulting urea undergoes hydrolysis.

SUMMARY OF THE INVENTION

An object of this invention is to provide a process of synthesizing urea in accordance with an improved stripping process which makes use of carbon dioxide.

Another object of this invention is to provide a process of synthesizing urea in accordance with an improved stripping process, which process consumes less high-pressure stem but is still capable of recovering low-pressure steam.

The present invention therefore provides a process of synthesizing urea including reacting ammonia and carbon dioxide at a urea synthesis pressure and temperature in a urea synthesis zone, separating excess ammonia and unreacted ammonium carbamate from the thus-obtained urea synthesis melt as a gaseous mixture containing ammonia and carbon dioxide, recirculating the gaseous mixture to the urea synthesis zone, and obtaining urea from an aqueous urea solution which has been obtained by separating the excess ammonia and unreacted ammonium carbamate, which process comprises the following consecutive steps:

(a) carrying out the synthesis of urea at temperatures of 170°–195° C. and pressures of 160–190 kg/cm²G and with a molar ratio of the total feed ammonia to the total feed carbon dioxide of 3.5–5.0 in the urea synthesis zone, and separating an inert gas containing oxygen and accompanied with ammonia and carbon dioxide at the same pressure as the urea synthesis pressure from the urea synthesis melt containing the thus-synthesized urea;

(b) subjecting the urea synthesis melt from the step (a) to a stripping operation including a rectification operation at the same pressure as the urea synthesis pressure and temperatures of 170°–205° C. using carbon dioxide which amounts to at least 60% of the make-up carbon dioxide supplied as a raw material for the synthesis of urea and contains 0.5–5.0% by volume of air as a corrosion inhibitor thereby decomposing and separating the unreacted ammonium carbamate together with gasified excess ammonia as a gaseous mixture of ammonia and carbon dioxide;

(c) subjecting the urea synthesis effluent from the step (b) to a medium-pressure decomposition operation at pressures in the range of 12–25 kg/cm²G so as to separate remaining ammonia and carbon dioxide from the urea synthesis effluent and obtain a urea solution containing still remaining ammonia and carbon dioxide in a total content of 5–12% by weight;

(d) reducing the pressure of the urea solution from the step (c) to a pressure of 1–5 kg/cm²G, thereby further separating at least parts of remaining ammonia and carbon dioxide from the urea solution and obtaining a mixed stream of another urea solution and a gas containing ammonia and carbon dioxide;

(e) heating the mixed stream obtained in the step (d) under the same pressure, subjecting the thus-heated mixed stream to an adiabatic stripping operation using carbon dioxide which amounts to 1–10% of the make-up carbon dioxide supplied as the raw material for the synthesis of urea to separate the majority of unreacted ammonia and carbon dioxide still remaining in the urea solution as a gas containing ammonia and carbon dioxide and obtain an aqueous urea solution substantially free of ammonia and carbon dioxide, and subjecting the aqueous urea solution to subsequent concentration and finishing steps:

(f) absorbing the ammonia and carbon dioxide separated in the step (e) in water, a dilute aqueous solution of ammonium carbonate or another aqueous urea solution, and absorbing in the thus-obtained aqueous solution as an absorbing medium the ammonia and carbon dioxide separated from the urea synthesis effluent in the step (c) at the same pressure as the medium-pressure decomposition step in the step (c);

(g) bringing the absorbate obtained in the step (f) and containing ammonia and carbon dioxide into contact with the gaseous mixture of ammonia and carbon dioxide separated in the step (b) at the same pressure as the urea synthesis pressure, condensing at least parts of ammonia and carbon dioxide in the gaseous mixture to such extents that the temperature in the urea synthesis zone is maintained within the predetermined temperature range, and removing the resulting heat of condensation; and then (h) recirculating the condensate and uncondensed gaseous mixture containing unreacted ammonia and carbon dioxide, both obtained in the step (g), to the urea synthesis zone in step (a).

In preferred embodiments, the present invention may include the following steps:

(i) The urea synthesis effluent obtained from the step (b) is subjected to a reduced-pressure flashing operation at the same pressure as the medium-pressure decomposition step in the step (c) and the medium pressure decomposition step in the step (c) is carried out by heating with the heat of absorption generated in the step (g) and, optionally, a steam heating, thereby decomposing and gasifying at least parts of unreacted substances;

(ii) Prior to reducing the pressure of the inert gas separated in the step (a), parts of the accompanying ammonia and carbon dioxide are washed with the pressurized absorbate from the step (f) and the resulting solution is used as the absorbent in the step (g), and then the inert gas is subjected to the treatment in the step (f);

(iii) The urea synthesis effluent obtained by the stripping operation in the step (b) is subjected to a heat exchange with the mixed stream obtained in the step (d);

(iv) The step (f) is carried out at temperatures of 80°–120° C. and at least part of the heat generated by the absorption of ammonia and carbon dioxide is utilized in the concentration step; and (v) The removal of generated heat of condensation in step (g) is carried out by producing steam of pressures in the range of 2–7 kg/cm$^2$G.

DETAILED DESCRIPTION OF THE INVENTION

Figure 1:
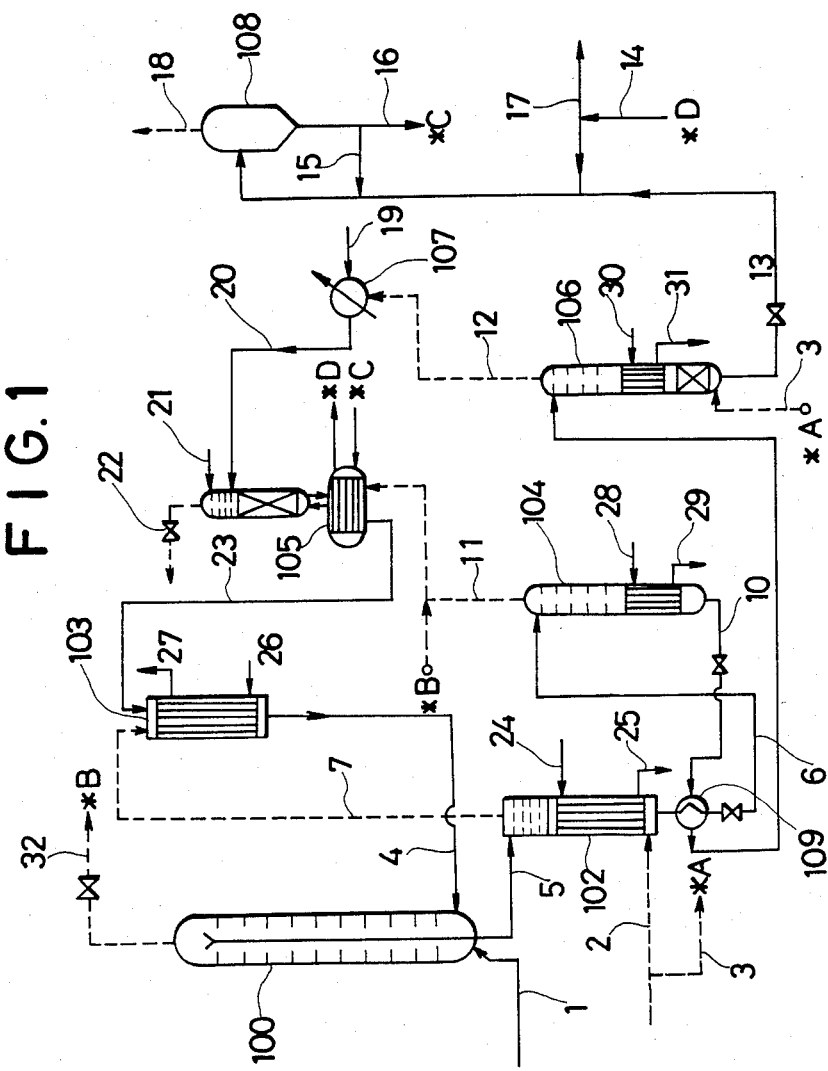
FIG. 1 is a flow sheet showing one embodiment of this invention in which embodiment no indirect heat exchange is conducted.

This invention is particularly suited for a urea synthesis process employing ammonia in a highly excess proportion, although it may also be applied to conventional urea synthesis processes which employ ammonia in slightly excess proportions. Generally speaking, the term "a urea synthesis process employing ammonia in a highly excess proportion" indicates a urea synthesis process in which the molar ratio of the total ammonia to the total carbon dioxide, both charged into a synthesis autoclave, is 3.5 or higher, and in many instances, is about 4. Here, the synthesis of urea is generally carried out under a pressure of from 200 to 250 kg/cm$^2$G and at a temperature of 190°–200° C. The synthesis ratio is as high as 65–72%. If one attempts to subject a urea synthesis melt obtained under the above conditions to a stripping operation under the same pressure as the urea synthesis pressure with a view toward decomposing and separating any unreacted substances, a temperature of at least 205° C. is indispensable. Since the high synthesis ratio was obtained owing to the presence of ammonia in a highly excess proportion, the hydrolysis of urea becomes easier to take place if a major portion of the ammonia is removed at temperatures higher than the urea synthesis temperature.

The forementioned various conditions of the present invention were found, as a result of an extensive investigation on the readiness of the stripping, the condensation temperature of the gaseous mixture from the stripping step and utilization of the heat of condensation, and the absorption temperature of the gaseous mixture from the medium-pressure decomposition step and the utilization of the resulting heat of absorption in the concentration step.

Namely, in step (a), the $NH_3/CO_2$ molar ratio is chosen from 3.5–5.0, while the condensation pressures for the gaseous mixture from the stripping step and the stripping pressure are individually selected from 160–190 kg/cm$^2$G. Any pressure lower than 160 kg/cm$^2$G does not provide any desired synthesis ratio and also fail to obtain any desired high condensation temperature for the gaseous mixture. On the other hand, if the pressure exceeds 190 kg/cm$^2$G, an inconvenience arises that use of a considerably high stripping temperature becomes indispensable.

The stripping temperature in step (b) is chosen from 170°–205° C. Below 170° C., the separation of unreacted substances cannot be effected to a desired extent, while the above-mentioned drawback such as hydrolysis arises at any temperatures beyond 205° C. The total content of ammonia and carbon dioxide in a urea synthesis effluent from the stripping step is normally selected from the range of from 14 to 30% by weight. Total contents below the lower limit are certainly desirable. However, such low total contents requires higher temperatures which lead to the above-described drawback, i.e., the hydrolysis of urea. If the total content exceeds the upper limit, far more heat is generated upon absorption of the gaseous mixture from the medium-pressure decomposition step than that required for the concentration step, thereby resulting in the consumption of more cooling water.

The rectification operation is carried out under adiabatic conditions or with mild cooling, prior to effecting the heated stripping operation. Owing to the inclusion of the rectification operation, a urea synthesis melt resulting from a urea synthesis process which employed ammonia in a highly excess proportion may be successfully subjected to a stripping operation, although the stripping of such a urea synthesis melt has heretofore been considered as a difficult operation. Namely, a part of excess ammonia present in the urea synthesis melt is caused to evaporate by the absorption heat of the stripping carbon dioxide, which flows up, prior to subjecting the urea synthesis melt to a heated stripping operation. As a result, the molar ratio of ammonia to carbon dioxide in the urea synthesis melt is lowered to such a value that permits an effective stripping operation with carbon dioxide gas. Accordingly, the effect of the rectification operation becomes greater as a higher molar ratio of ammonia to carbon dioxide is employed in the synthesis of urea.

The amount of carbon dioxide employed for the stripping operation amounts to at least 60% of the quantity of carbon dioxide to be supplied as a urea synthesis raw material, namely, the make-up carbon dioxide, because the synthesis of urea is carried out with an excess amount of ammonia. The effect of the stripping operation is considerably reduced if less carbon dioxide is employed in the stripping operation. The carbon dioxide, used in the stripping operation, contains air which serves as a corrosion inhibitor.

Air, which serves to protect the stripper, carbamate condenser and synthesis autoclave from corrosion, is in advance mixed in carbon dioxide to be charged as a raw material for the synthesis of urea and introduced into a lower part of the stripper. The proportion of air may range from 0.5 to 5.0% by volume based on the resulting gaseous mixture. Any proportions smaller than the lower limit cannot exhibit enough anti-corrosive effect. On the other hand, even if air is used in any amounts more than the upper limit, its anti-corrosive effect will not be enhanced. On the contrary, use of such excess air leads to such drawbacks that the synthesis yield of urea is lowered and it is accompanied by lots of ammonia and carbon dioxide gas when separated as the inert gas is the step (a), resulting in larger facilities for the treatment of the inert gas. In order to decrease the volume of water to be evaporated by the reduced-pressure flashing in the medium-pressure decomposition zone as much as possible, the urea synthesis effluent resulting from the stripping operation is in some instances subjected to a heat exchange with a mixed stream obtained from the medium-pressure decomposition operation prior to reducing the pressure of the urea synthesis effluent to the pressure of the medium-pressure decomposition step of the step (c). The effect of the heat-exchange becomes greater as the stripping temperature goes higher. The heat exchange eventually serves to reduce the volume of water accompanying ammonia and carbon dioxide to be recirculated to the urea synthesis zone, thereby contributing to an improvement in the synthesis ratio of urea. However, the effect derived from cooling the urea synthesis effluent, which is to be subjected to medium-pressure decomposition, tends to become smaller as the temperature of the urea synthesis effluent drops after its cooling. Generally speaking, no more effect may be expected even if the urea synthesis effluent is cooled further than it is cooled by the above heat-exchange operation.

The pressure of the medium-pressure decomposition operation in the step (c) in which the urea synthesis effluent from the stripping step is subjected to decomposition may range from 12 to 25 kg/cm$^2$G. Below the lower limit, it is impossible to raise the absorption temperature for the gaseous mixture from the medium-pressure decomposition operation beyond 80° C. Accordingly, the resulting heat of absorption cannot be utilized in the concentration step. Furthermore, another problem arises that ammonium carbamate may be deposited in the solvent after absorption. On the other hand, any pressures higher than the upper limit require to conduct the medium-pressure decomposition operation at still higher temperatures, which result in such unfavorable problems as increased hydrolysis of urea and abundant formation of biuret.

In the medium-pressure decomposition operation, the urea synthesis effluent may be subjected to decomposition while maintaining its temperature, for example, within 160°–170° C. with steam if necessary so that the total content of the ammonia and carbon dioxide still remaining in the urea synthesis effluent discharged form the medium-pressure decomposition step ranges from 5 to 12% by weight. If the steam heating temperature is too low or the urea synthesis effluent contains too much unreacted substances, the absorption of the gaseous mixture from the medium-pressure decomposition operation in the medium-pressure absorption column is unable to generate sufficient heat of absorption, thereby failing to cover the heat required in the concentration step.

Incidentally, it is preferable to conduct the medium-pressure absorption operation at 80°–120° C. Below the lower limit, certain problems arise including reduction in cooling efficiency due to the deposition of ammonium carbamate and development of localized clogging. On the other hand, any temperatures higher than the upper limit result in insufficient absorption. In addition, use of such higher temperatures makes operations in the recovery system after the low-pressure decomposition unit, for example, the absorbing operation difficult.

In the medium-pressure heating operation, the heating is not entirely effected by external steam heating. At least part of the heating is effected by subjecting the urea synthesis effluent to an indirect heat exchange with the heat of absorption generated in the condensor of the step (g). Namely, it is possible to divide the condenser into equal halves and to use one half as a heater for the medium-pressure decomposition operation. This enables to save at least part of the high-pressure steam to be supplied for the medium-pressure decomposition from an external source. At the same time, this decreases the volume of low-pressure steam to be recovered in the condenser. Although success of the above heating method is dependent on the relationship between the operational conditions of the stripper and condenser and those of the medium-pressure decomposition operation, it becomes more advantageous as the difference in operation pressure between the stripper and condenser and the medium-pressure decomposition operation increases.

The operation pressures in the steps (d) and (e) may preferably range from 1–5 kg/cm$^2$G individually. Below the lower limit, a large amount of an absorbing medium such as water, a dilute aqueous solution of ammonium carbonate or an aqueous urea solution is required when absorbing ammonia and carbon dioxide gas separated in the steps (d) and (e) under the same pressure, in other words, in the so-called low-pressure absorbing operation. As a result, a large volume of water is introduced into the synthesis zone, leading to a considerable drop in the synthesis yield. On the other hand, above the upper limit, high temperatures are required if one attempts to separate unreacted substances as much as possible. Use of such high temperatures results in such demerits that the hydrolysis of urea and formation of biuret are promoted and the steam generated in the step (g) cannot be used. In the low-pressure decomposition step of the step (e), the stripping operation is carried out under adiabatic conditions using carbon dioxide which constitutes 1–10% of the carbon dioxide fed as a raw material for the synthesis of urea so that the ammonia remaining in the urea solution can be decreased in quantity as much as possible and, since the carbon dioxide gas introduced into the low-pressure decomposition region in the above stripping operation serves to lower the partial pressure of ammonia in the low-pressure unreacted substance recovery zone operated at the same pressure as the low-pressure decomposition zone, the volume of water as the absorbing medium in the low-pressure unreacted substance recovery zone can be decreased as a result. This decrease in the volume of water as the absorbing medium in the low-pressure unreacted substance recovery zone leads to a decrease in the volume of water accompanying unreacted ammonia and carbon dioxide to be delivered to the urea synthesis zone, thereby, as a result, bringing about an effect to improve the synthesis ratio of urea.

The above stripping operation is carried out under adiabatic conditions with a view toward lowering the temperature of the urea solution, from which ammonia has been stripped, and suppressing the formation of undesirable biuret. If carbon dioxide is used in any amounts smaller than its lower limit in the stripping operation, no noticeable stripping effect is available. On the other hand, if carbon dioxide exceeds its upper limit, it brings about such disadvantages that ammonium carbamate is caused to deposit in the low-pressure unreacted substance recovery zone and the heat of absorption of carbon dioxide is less effectively utilized. The above disadvantages are greater than the stripping effect of carbon dioxide. Thus, it is preferred to use carbon dioxide within the above-described range.

As the absorbent employed in the low-pressure absorbing operation in the step (f), may be used water, a dilute aqueous solution of ammonium carbonate or an aqueous urea solution. The aqueous urea solution from the step (e) still contains not more than 1% of unreacted ammonia and carbon dioxide. These unreacted substances are separated in the concentration and finishing steps which follow the step (e) and are temporarily recovered as a dilute aqueous solution of ammonium carbonate. Normally, only a part, i.e., a desired amount of the aqueous solution of ammonium carbonate is used directly as the absorbent for the low-pressure absorption and the remainder is subjected to its concentration operation and then fed into the low-pressure absorption zone. However, when a urea product of a biuret content of 0.3% or less is desired, urea is crystallized under vacuum from the aqueous urea solution from the step (e) and biuret is left in the mother liquor. Since the thus-obtained mother liquor is an aqueous urea solution practically free of ammonia and carbon dioxide, it can be used as the absorbent for low-pressure absorption. However, the aqueous urea solution to be employed as the absorbent for low-pressure absorption is not limited to the above mother liquor. For example, it may be possible to use an aqueous urea solution which has been obtained by recovering those scattered around as the so-called urea mist or urea powder in the concentration and finishing steps in the form of an aqueous solution. When using aqueous urea solution as the absorbent for the low-pressure absorption as described above, the aforementioned recovered dilute aqueous solution of ammonium carbonate is introduced into the low-pressure absorption zone after subjecting it in its entirety to a concentration operation. Therefore, it is more often to use water for washing the inert gas which has built up in the low-pressure absorption zone rather than to use the same singly as an absorbent. The above practice is adopted in order to recover accompanying ammonia and carbon dioxide upon disposing of the inert gas.

It is preferred to choose a temperature higher by at least 5° C. than the saturation temperature for the pressure of produced steam as the condensation temperature for the gaseous mixture from the above-described stripping step which is carried out under the same pressure as the urea synthesis pressure, when the removal of the heat of condensation is effected in the form of steam generation. For example, when the steam saturation temperature is 155° C., it is preferred to raise the condensation temperature for the gaseous mixture to 160° C. or higher.

The volumes of ammonia and carbon dioxide to be condensed in the carbamate condenser are determined by the intended temperature of the urea synthesis melt to be obtained in the urea synthesis zone. Namely, once the synthesis pressure, the ratio of the total ammonia to total carbon dioxide and the ratio of water to the total carbon dioxide in the urea synthesis zone have been set, the composition of the resulting urea synthesis melt is substantially determined by the temperature in the urea synthesis zone. On the other hand, the temperature in the urea synthesis zone is maintained at substantially the same level by the heat given off upon formation of ammonium carbamate from ammonia and carbon dioxide. Therefore, the volumes of ammonia and carbon dioxide to be condensed in the carbamate condenser are adjusted using the intended temperature of the urea synthesis melt as an index. Namely, when the temperature in the synthesis zone is higher than the predetermined target temperature, more ammonia and carbon dioxide are condensed. On the other hand, less ammonia and carbon dioxide are subjected to condensation if the temperature in the synthesis zone is lower than the target temperature. By the way, it is desirable to obtain steam of a pressure in the range of 2–7 $kg/cm^2G$. Any pressure lower than the lower limit results in such steam that has no usable value or only limited use, because such steam undergoes condensation at low temperatures. On the other hand, pressures higher than the upper limit are certainly preferred if feasible. However, in view of urea synthesis conditions, the pressure increase is limited to only 2–3 $kg/cm^2G$ above the upper limit even if succeeded to do so. If one wants to obtain steam of such a high pressure on the industrial scale, he will face the development of a corrosion problem and the requirement for a condenser having an excessively large heat transfer area. On the other hand, steam of a pressure within the above range is satisfactorily employed in the majority of steam-consuming steps of a urea synthesis process. Thus, the upper limit has been set at 7 $kg/cm^2G$.

When the temperature in the step (a) is relatively high in view of the pressure in the same step, it is effective to partly wash the inert gas, which has been separated in the step (a) and contains ammonia and carbon dioxide accompanying therewith, with the pressurized solution from the step (f) prior to depressurizing the inert gas to the pressure of the step (f). Namely, a high synthesis temperature leads to more ammonia and carbon dioxide accompanying the inert gas and thus to an increased heat loss in the step (f). By following the above method, it is possible to avoid such a heat loss. Since only a part of the inert gas is subjected to the washing, the gaseous mixture obtained after the washing does not involve any danger of explosion.

According to this invention, various conditions of process steps are ingeniously combined together so as to produce urea using less high-pressure steam and recovering less low-pressure steam. The following are specific examples of effects which the present invention can bring about.

(1) A stripping operation making use of carbon dioxide can be effectively incorporated in a urea synthesis process employing ammonia in a highly excess proportion, although such a combination has heretofore been considered a difficult one to practice;

(2) In the conventional urea synthesis process making use of the stripping process, the consumption of high-pressure steam and the recovery of low-pressure steam were both high. (A process has been considered to be better as the difference between the consumption of high-pressure steam and the recovery of low-pressure steam becomes smaller.) In the present invention, it has been succeeded to reduce the volume of high-pressure steam required for stripping because the process according to this invention enjoys a high synthesis ratio of urea and the stripping of a urea synthesis melt containing ammonia in an excess proportion has become feasible. Accordingly, the present invention has solved the drawbacks of the prior art urea synthesis processes making use of the stripping operation that valuable high-pressure steam is used in a large amount and, instead, low-pressure steam having a low value is recovered in a large amount. In addition, it is possible to reduce the volume of the feed high-pressure steam where the medium-pressure decomposition operation is carried out by a direct heat exchange with the carbamate condenser; and (3) The construction cost of the plant can be reduced. Namely, by decomposing and separating unreacted substances first by stripping and then by the medium-pressure decomposition at 12–25 kg/cm²G, it has become possible to carry out the operation of the stripping step under milder conditions compared with the prior art technique, without decreasing the recovered heat. Moreover, owing to the inclusion of the medium-pressure absorbing operation, it has become easier to effect the washing of the inert gas from the urea synthesis zone. As a result, it has become possible to make the volumes of high-pressure equipments in the urea synthesis zone smaller.

In addition, it is possible in the present invention to make the pressure of the medium-pressure decomposition step lower than the absorption pressure for the gaseous mixture obtained in the medium-pressure decomposition step and to effect the absorption of the gaseous mixture from the medium-pressure decomposition step after raising its pressure to the absorbing pressure. Since the above method permits to make the medium-pressure decomposition pressure still lower, low-pressure steam generated in the process may in some instances be used as a heat source for the medium-pressure decomposition step. Because the absorption pressure for the gaseous mixture from the medium-pressure decomposition step can be set freely independent from the pressure of the medium-pressure decomposition step and a high pressure convenient for the absorption may be chosen, it is possible to raise the absorbing temperature. This makes the utilization of this heat of absorption easier.

One embodiment of this invention will hereinafter be described in the following examples, making reference to the accompanying drawings.

EXAMPLE 1

An experiment was carried out in accordance with the flow sheet shown in FIG. 1. Charged into a urea synthesis autoclave 100 were 568 kg/hr of liquid ammonia through a line 1 and, as a gas-liquid mixture of 165° C., 1267 kg/hr of ammonia, 1129 kg/hr of carbon dioxide and 265 kg/hr of water through a line 4. The urea synthesis autoclave 100 was operated at the pressure of 185 kg/cm²G and the temperature of 192° C. and with the residence time of about 1 hour. With the synthesis ratio of 69%, a urea synthesis melt consisting of 1042 kg/hr of urea, 1118 kg/hr of ammonia, 340 kg/hr of carbon dioxide and 570 kg/hr of water was obtained. In the meantime, a gaseous mixture containing an inert gas (ammonia 127 kg/hr; carbon dioxide 25 kg/hr; and water 7 kg/hr) was purged from the top of the urea synthesis autoclave 100, through a line 32, and fed to a lower part of a medium-pressure absorbing column. The above urea synthesis melt was introduced through a line 5 into the top of a rectification zone formed of several stages of sieve trays in a stripper 102 of the same pressure. The urea synthesis melt was countercurrently contacted with an upward flow of a gaseous mixture containing ammonia, carbon dioxide and water while flowing down through the rectification zone, thereby exchanging the excess ammonia in the urea synthesis melt with the carbon dioxide in the gaseous mixture and adjusting the ratio of the ammonia to the carbon dioxide in the urea synthesis melt to a value within a readily strippable range at the bottom of the rectification zone. Thereafter, while the urea synthesis melt is caused to flow down through a falling-film heating tube, unreacted substances were stripped off from the urea synthesis melt by its heating with high-pressure steam of 25 kg/cm²G, which was applied through a line 24 and discharged through a line 25, and 676 kg/hr of pressurized carbon dioxide gas (160° C.) charged through a line 2. From the bottom of the stripper 102, was obtained at the temperature of 198° C. a solution consisting of 1019 kg/hr of urea, 205 kg/hr of ammonia, 201 kg/hr of carbon dioxide and 494 kg/hr of water.

The above solution immediately entered a heat exchanger 109 and subjected to a heat exchange with a depressurized urea solution from a medium-pressure decomposition zone which will be described later. The thus heat exchanged solution was thereafter depressurized and flashed to 18 kg/cm²G through a line 6 to introduce into a medium-pressure decomposition column 104. The flashing temperature was 145° C. The medium-pressure decomposition column 104 was formed of several stages of sieve trays and a heater disposed below the sieve trays. It was heated by high-pressure steam which was supplied through a line 28 and discharged through a line 29 so as to separate unreacted substances to predetermined levels. After the separation of unreacted substances, the solution had a composition consisting of 1008 kg/hr of urea, 100 kg/hr of ammonia, 33 kg/hr of carbon dioxide and 460 kg/hr of water. This solution was depressurized to 2 kg/cm$^2$G through a line 10, fed through the shell side of the above-described heat exchanger 109, and subjected to successive treatments in a low-pressure decomposition column 106 and vacuum concentrator (crystallizer) 108. By the way, the low-pressure decomposition column 106 was supplied with 58 kg/hr of carbon dioxide introduced as a stripping medium through a line 3. On the other hand, a separated gas was guided from the medium-pressure decomposition column 104, through a line 11, and to a lower part of a medium-pressure absorption column 105 of 17.5 kg/cm$^2$G, together with the purge gas fed through the line 32 from the urea synthesis autoclave 100. Most of the separated gas was absorbed at 100° C. in the medium-pressure absorption column 105. The heat of absorption, generated there, was removed by a urea slurry fed through a line 16 from the crystallizer 108. The urea slurry contained a little crystals and had the temperature of 65° C. Out of the thus-heated urea slurry in a line 14, an amount corresponding to the urea product, i.e., 1124 kg/hr was delivered to a finishing step through a line 17. The remainder was returned to the crystallizer 108 and a necessary amount of its water was caused to evaporate there. The recovered heat was equivalent to 150 kg/hr of low-pressure steam. A slight amount of unabsorbed gas, which was present in a lower part of the medium-pressure absorbing column (cooler), was allowed to rise through a packed layer of the medium-pressure absorption column. In the course of its rise, it was absorbed in an aqueous solution of ammonia and carbon dioxide introduced through the line 20 from the low-pressure absorbed (ammonia 103 kg/hr; carbon dioxide 96 kg/hr; and water 148 kg/hr) and 15 kg/hr of water introduced through a line 21, and caused to drop into the cooling part. Thus, only inert gas was purged from the top of the column through a line 22. From the cooler below the medium-pressure absorption column, was obtained a solution which consisted of 341 kg/hr of ammonia, 297 kg/hr of carbon dioxide, and 196 kg/hr of water.

This solution was pressurized to 185 kg/cm$^2$G and then fed through a line 23 to a carbamate condenser 103, in which a part of the gaseous mixture (ammonia 926 kg/hr; carbon dioxide 832 kg/hr; and water 69 kg/hr) of 195° C. from the stripper 102 was condensed and absorbed so as to make the urea synthesis melt from the urea synthesis autoclave 100 have a preset temperature. The heat generated by the absorption was recovered as low-pressure steam of 4 kg/cm$^2$G. After the absorption, the temperature of the solution reached 165° C. as described above. The absorbate was recirculated together with a part of unabsorbed gas as a gas-liquid mixture to the urea synthesis autoclave 100. The amount of the recovered low-pressure steam was 680 kg/hr. Out of 680 kg/hr, 400 kg/hr was used in the low-pressure decomposition column and the finishing step as well as for recovering slight amounts of ammonia and carbon dioxide contained in the evaporated water (line 18) from the vacuum concentrator. 280 kg/hr was a surplus and was drawn out of the urea process. As a result, since 820 kg/hr of high-pressure steam was used principally in the stripper and medium-pressure decomposition column, the above urea synthesis process consumed 540 kg/hr of steam in total.

EXAMPLE 2

Figure 2:
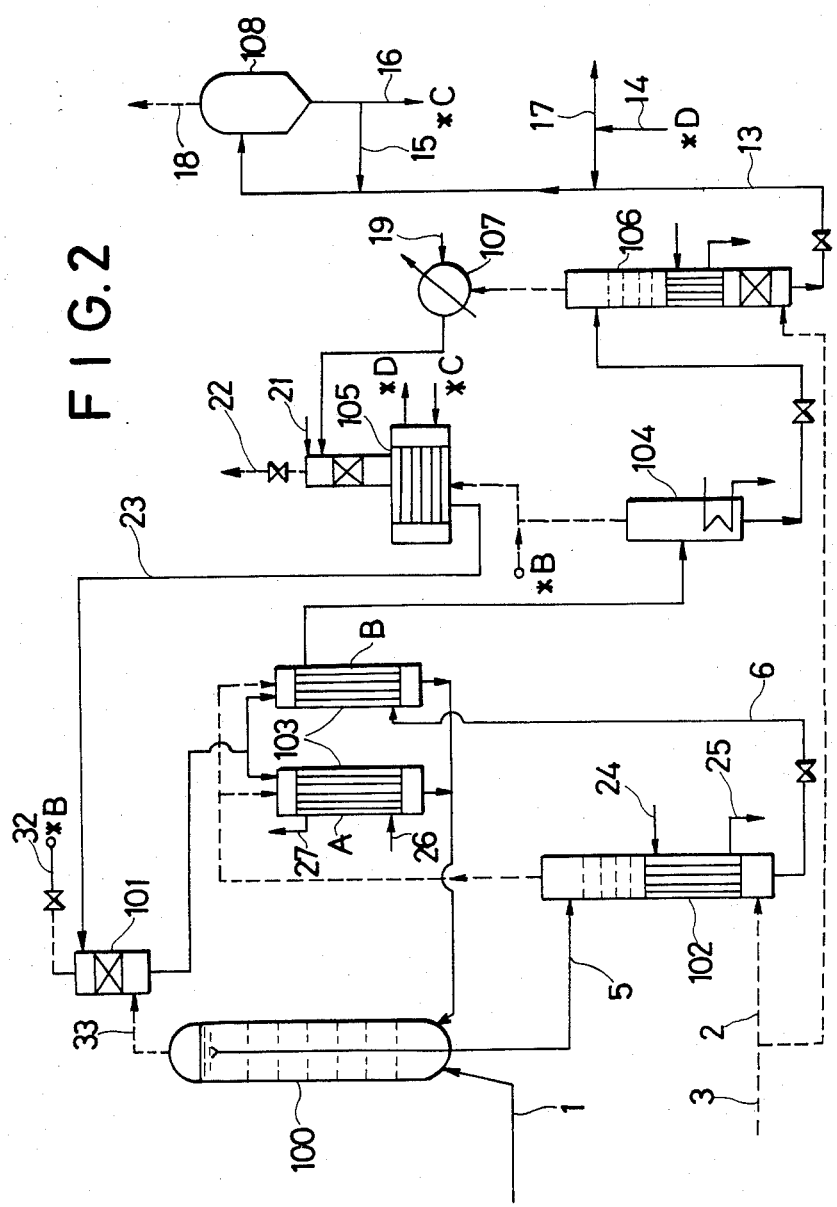
FIG. 2 is a flow sheet illustrating another embodiment of this invention in which embodiment an indirect heat exchange is conducted and an inert gas scrubber is additionally provided.

Another experiment was conducted in accordance with the flow sheet illustrated in FIG. 2. This example was carried out under the same conditions as Example 1 except for the following matter.

The urea synthesis effluent, which had been subjected to the stripping operation of the step (b), was immediately depressurized and flashed to 18 kg/cm$^2$G and then introduced to one of the columns, i.e., the shell side 103B of the carbamate condenser. Parts of unreacted substances in the urea synthesis effluent were decomposed further in the tube side by heat generated owing to the formation of carbamate. The urea synthesis effluent was thereafter introduced into the medium-pressure decomposition column 104 equipped with a steam-heated part. Treatments in the medium-pressure decomposition column and its subsequent units were conducted in the same manner as in Example 1.

A gaseous mixture consisting of 127 kg/hr of ammonia, 25 kg/hr of carbon dioxide, 7 kg/hr of water and the inert gas separated in the step (a) was introduced through a line 33 into an inert gas washing column 101 in which the gaseous mixture was washed with a pressurized solution fed from the step (f) through a line 23. As a result, the gaseous mixture discharged from the inert gas washing column 101 contained 49 kg/hr of ammonia, 25 kg/hr of carbon dioxide and 5 kg/hr of water and depressurized to the pressure in the step (f) and introduced into the medium pressure absorption column 105 through a line 32 to be treated in the same manner as in Example 1. Enthalpy of the solution from the inert gas washing column 101 increased resulting in increasing the amount of steam generated in step (g).

As a result of the above operations. the steam generated in the step (g) was increased by 58 kg/hr. Correspondingly, the heat generated in the step (f) was decreased on the contrary. Owing to these operations, the consumption of high-pressure steam, which was mainly used in the stripper and high-pressure decomposition column, became smaller than that used in Example 1, i.e., was decreased to 670 kg/hr. On the other hand, the low-pressure steam generated in the carbamate condenser was decreased. As a result, the surplus low-pressure steam was decreased to 188 kg/hr. Therefore, the above urea synthesis process required 482 kg/hr of steam in total.

What is claimed is:

1. In a process for synthesizing urea, including the steps of:
   (a) in a urea synthesis zone, reacting ammonia and carbon dioxide, at a pressure of 160–190 kg/cm$^2$G and a temperature of 170°–195° C., while maintaining the molar ratio of the total ammonia to the total carbon dioxide in said urea synthesis zone in the range of 3.5–5.0, whereby to obtain a urea synthesis melt containing urea, ammonium carbamate and excess ammonia;
   (b) subjecting said urea synthesis melt to a stripping operation using carbon dioxide as a stripping gas, the amount of carbon dioxide supplied as a stripping gas being at least 60 % of the make-up amount of carbon dioxide that is needed to make up for the carbon dioxide consumed in the process, the stripping operation being carried out at the same pressure as the pressure in said urea synthesis zone and at a temperature of 170°–205° C. whereby to decompose ammonium carbamate in said melt, separating a first gas containing carbon dioxide and ammonia from said melt and thereby obtaining a first urea synthesis effluent containing ammonia and carbon dioxide;

(c) subjecting said first urea synthesis effluent to a medium-pressure decomposition at a pressure of 12–25 kg/cm$^2$G, separating a second gas comprising a part of the ammonia and carbon dioxide that was contained in said first effluent and recovering a second urea synthesis effluent in which the sum of the amounts of ammonia and carbon dioxide contained therein is from 5–12% by weight;

(d) subjecting said second urea synthesis effluent to low temperature decomposition to separate a third gas containing ammonia and carbon dioxide and to obtain a first aqueous urea solution substantially free of ammonia and carbon dioxide;

(e) subjecting said first aqueous urea solution to concentration and finishing steps;

(f) absorbing said third gas containing ammonia and carbon dioxide that was separated in step (d) in water, a dilute aqueous solution of ammonium carbonate or a second aqueous urea solution, whereby to obtain a first aqueous absorption liquid, and then absorbing said second gas containing ammonia and carbon dioxide that was separated in step (c) in said first aqueous absorption liquid, at the same pressure as the pressure in step (c), whereby to obtain a second aqueous absorption liquid;

(g) contacting said second aqueous absorption liquid with said first gas that was separated in step (b) at the same pressure as the pressure in said urea synthesis zone, condensing at least part of the ammonia and carbon dioxide contained in said first gas in order to maintain the temperature in said urea synthesis zone in the range of 170°–195° C., removing the resulting heat of condensation and using at least some of said heat of condensation to effect the decomposition in step (c), and obtaining a mixture of said second aqueous absorption liquid, condensate and uncondensed ammonia and carbon dioxide; and (h) recirculating said mixture to said urea synthesis zone in step (a); the improvement which comprises:

in step (b), prior to said stripping operation, said urea synthesis melt is first subjected to rectification in order to reduce the ammonia concentration of said melt and thereby adjust the ratio of NH$_3$ to CO$_2$ of said melt before said melt is subjected to said stripping step, and, in step (d), the low temperature decomposition is effected by reducing the pressure of said second urea synthesis effluent to 1–5 kg/cm$^2$G and thereby transforming said second effluent to a mixed stream of a third aqueous urea solution and a fourth gas containing ammonia and carbon dioxide which fourth gas is separated from said second effluent by the reduction in pressure, then subjecting said mixed stream to adiabatic stripping using carbon dioxide as a stripping gas, the amount of carbon dioxide used in said adiabatic stripping being from 1–10% of the said make-up amount of carbon dioxide, thereby separating said third gas containing ammonia and carbon dioxide and obtaining said first aqueous urea solution substantially free of ammonia and carbon dioxide.

2. The process as claimed in claim 1 including the steps of separating a fifth, inert gas containing ammonia and carbon dioxide from said urea synthesis zone, washing said fifth gas with said second aqueous absorption liquid from step (f) prior to feeding said second aqueous absorption liquid to step (g), and mixing the washed fifth gas with said second gas that was separated in step (c) prior to feeding same to step (f).

3. The process as claimed in claim 1 in which between steps (b) and (c), the first urea synthesis effluent is flowed in indirect heat exchange relationship with said mixed stream obtained in step (d).

4. The process as claimed in claim 1, claim 2 or claim 3 in which step (f) is carried out at a temperature of 80°–120° C. and at least part of the heat generated by the absorption of ammonia and carbon dioxide is utilized to concentrate said first aqueous urea solution.

5. The process as claimed in claim 1, claim 2 or claim 3 wherein the step of removing the resulting heat of condensation in step (g) is carried out by generating steam having a pressure of 2–7 kg/cm$^2$G.

* * * * *